United States Patent [19]
Krueger et al.

[11] Patent Number: 5,578,076
[45] Date of Patent: Nov. 26, 1996

[54] LOW PROFILE HOLDER FOR HEART VALVE PROSTHESIS

[75] Inventors: Kurt D. Krueger, Stacy; Guy Vanney, Blaine, both of Minn.

[73] Assignee: St. Jude Medical, Inc., St. Paul, Minn.

[21] Appl. No.: 449,145

[22] Filed: May 24, 1995

[51] Int. Cl.⁶ .................... A61F 2/24; A61M 1/10
[52] U.S. Cl. ...................... 623/2; 623/900; 606/1
[58] Field of Search ................... 623/2, 900, 66; 606/1

[56] References Cited

U.S. PATENT DOCUMENTS

| | | |
|---|---|---|
| 3,828,787 | 8/1974 | Anderson et al. . |
| 3,860,005 | 1/1975 | Anderson et al. . |
| 4,655,218 | 4/1987 | Kulik et al. . |
| 4,683,883 | 9/1987 | Martin . |
| 4,755,181 | 7/1988 | Igoe . |
| 4,865,600 | 9/1989 | Carpenter et al. . |
| 4,932,965 | 6/1990 | Phillips . |
| 5,236,450 | 8/1993 | Scott . |
| 5,370,685 | 12/1994 | Stevens . |
| 5,403,305 | 4/1995 | Sauter et al. ................... 623/2 |
| 5,443,502 | 8/1995 | Caudillo et al. ............... 623/900 |

FOREIGN PATENT DOCUMENTS

| | | |
|---|---|---|
| 1690738 | 4/1989 | U.S.S.R. . |
| 1690739 | 11/1991 | U.S.S.R. ................... 623/2 |
| 9117720 | 11/1991 | WIPO . |
| 9418881 | 9/1994 | WIPO . |
| W095/15715 | 6/1995 | WIPO . |
| 9517139 | 6/1995 | WIPO . |

Primary Examiner—John G. Weiss
Assistant Examiner—Bruce E. Snow
Attorney, Agent, or Firm—Hallie A. Finucane

[57] ABSTRACT

A device for engaging a heart valve prosthesis during implantation includes a handle and a low profile holder. The handle has a proximal end and a distal end. The distal end is attached to the low profile holder which includes a distal engaging surface adapted for engaging the heart valve prosthesis. The distal engaging surface of the low profile holder maintains a leaflet of the heart valve in a closed position during implantation. This provides a low profile to the heart valve and holder which facilitates insertion through a trocar in a patient.

27 Claims, 14 Drawing Sheets

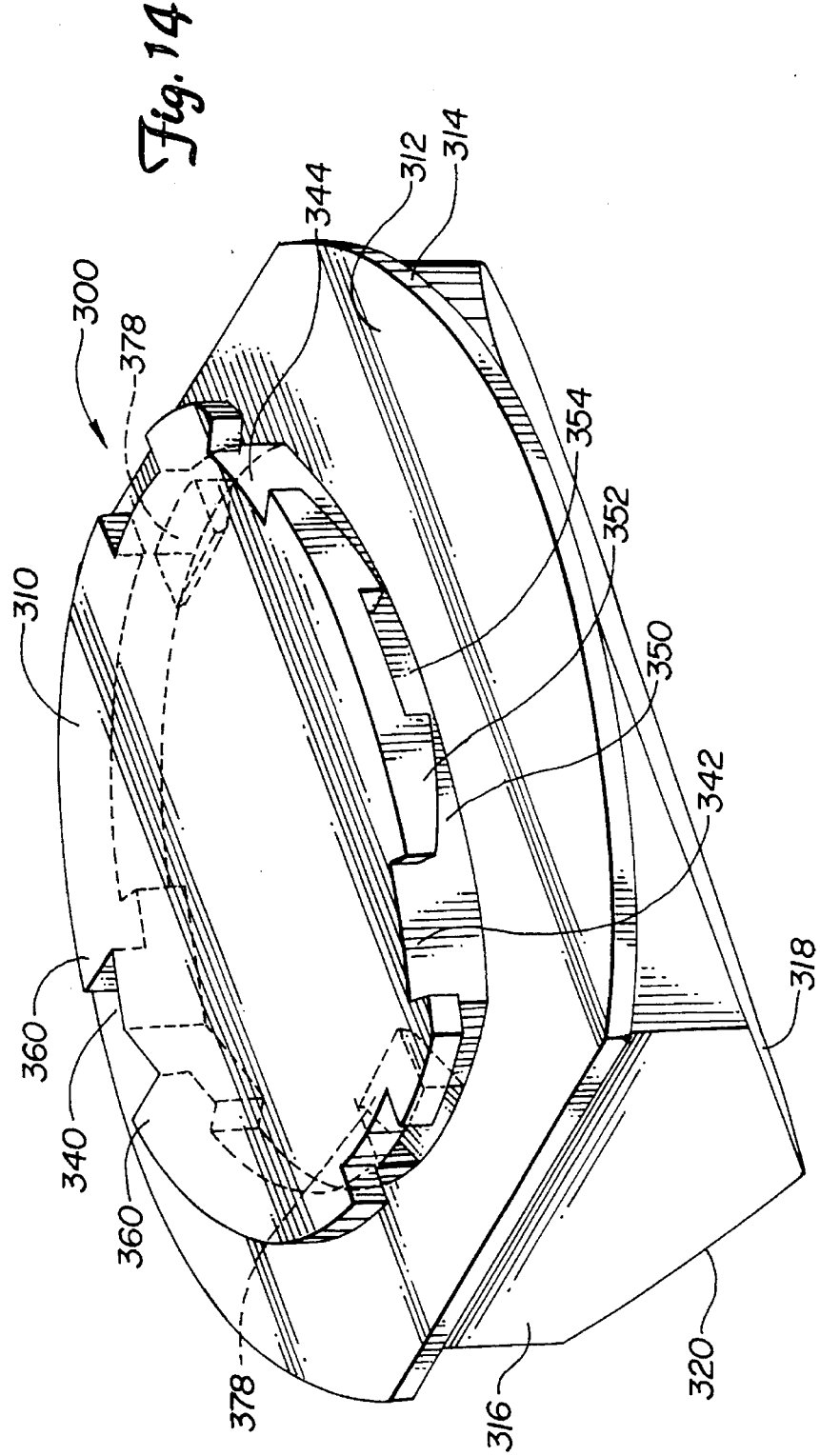
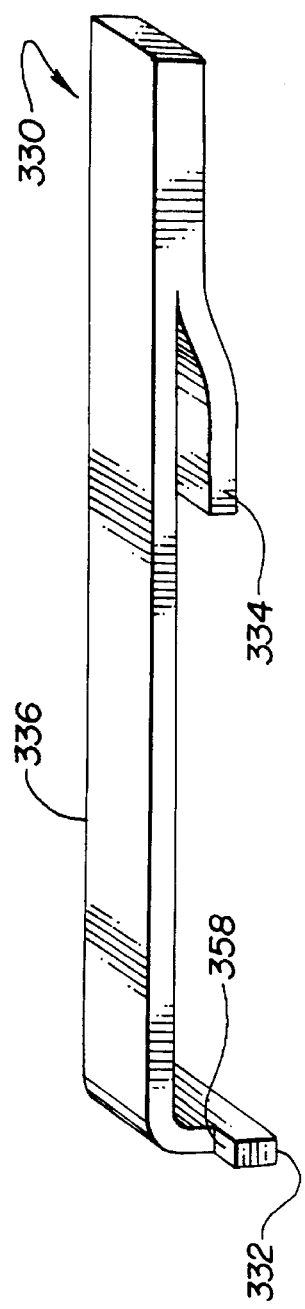

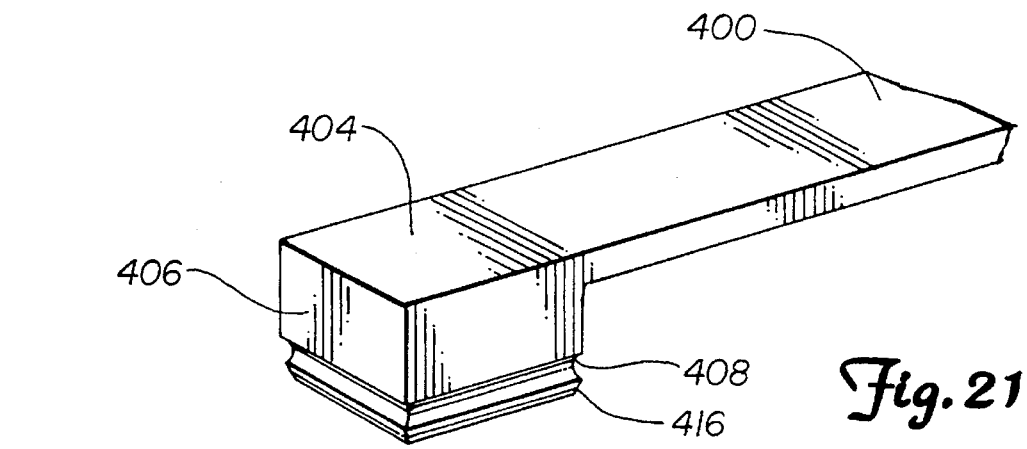
Fig. 21
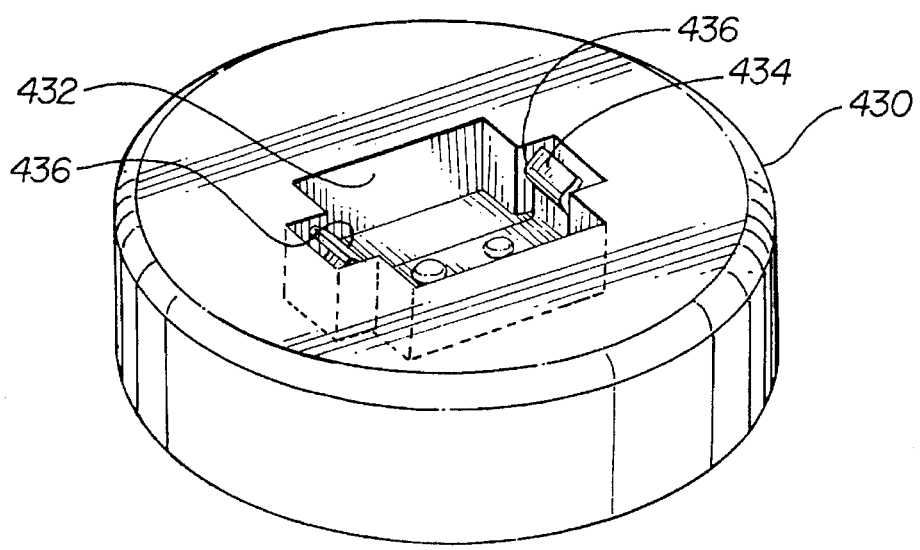
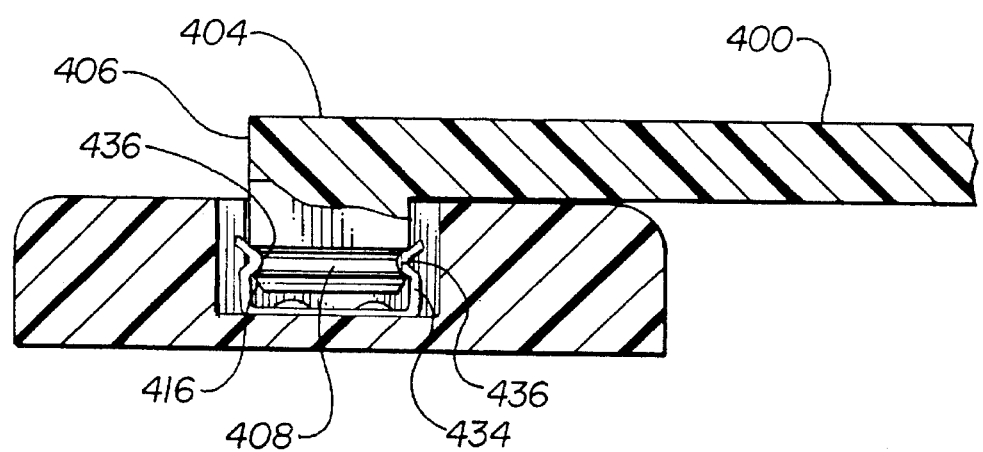
Fig. 22

5,578,076

LOW PROFILE HOLDER FOR HEART VALVE PROSTHESIS

FIELD OF THE INVENTION

The present invention relates to devices for implanting heart valve prostheses. More specifically, the invention relates to a low profile holder for holding a heart valve prosthesis during implantation.

BACKGROUND OF THE INVENTION

Holders for holding heart valve prostheses during implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Typically, heart valve replacement surgery is an involved procedure in which a sternotomy or thoracotomy is performed and the chest cavity of the patient must be widely opened to provide access to the patient's heart. This provides a surgeon with direct, unobstructed access to the heart. However, this procedure requires a prolonged period to recover from the trauma suffered to the upper torso.

Recently, a procedure has been developed wherein open heart surgery is performed through trocars placed in small incisions between two ribs of the patient. This is described in International Publication No. WO 94/18881, entitled METHOD FOR PERFORMING THORASCOPIC CARDIAC BYPASS PROCEDURES. In this procedure, elongated tools are used to operate on the heart through the trocars. As discussed in Publication No. 94/18881, this procedure can be used during heart valve replacement.

The trocar requires minimal rib spreading and does not involve the significant chest trauma associated with traditional open heart surgery. One advantage of this procedure is that the recovery period can be reduced significantly. Unfortunately, mechanical heart valves and the associated assembly used for implantation are large relative to the trocar and are difficult to fit therethrough. Further, the delicate valve leaflets protrude from the prosthesis and may be damaged during insertion through the narrow trocar.

SUMMARY OF THE INVENTION

A device for engaging a heart valve prosthesis during implantation includes a handle and a low profile holder. The heart valve prosthesis has an annulus with a substantially annular aperture therein and at least one leaflet movable between an open position and a closed position. The handle includes a proximal end and a distal end. The low profile holder has a proximal surface attached to the distal end of the handle and a distal engaging surface adapted for engaging the heart valve prosthesis. The distal engaging surface maintains the leaflet in a closed position during implantation of the heart valve prosthesis. The proximal surface of the low profile holder and an axis of the handle are substantially parallel to the annulus of the valve and perpendicular to the axis of the valve. This configuration facilitates insertion of the valve and low profile holder through a trocar in a patient during implantation of the valve.

Embodiments include mitral and aortic heart valve holder mechanisms for attaching the handle to the holder, and a hanger for carrying the holder in packaging.

BRIEF DESCRIPTION OF THE DRAWINGS

FIG. 14 is a top perspective view of a holder in accordance with another embodiment.

FIG. 15 is a plan view of a handle adapted for attachment to the holder of FIG. 14.

FIG. 21 is an exploded perspective view showing attachment of a handle to a holder in accordance with another embodiment.

FIG. 22 is a cross-sectional view of the embodiment of FIG. 21.

DETAILED DESCRIPTION OF THE PREFERRED EMBODIMENTS

The invention relates to a device which is a low profile prosthetic heart valve holder used to position a heart valve prosthesis during implantation. Preferably, this implantation is through minimally invasive surgery such as when performed through a small trocar between two ribs of the patient. The holder and valve are carried at the distal end of a handle which extends perpendicular to an axis of the valve annulus during insertion through the trocar. For purposes of this description of the invention, the holder will be described generally with regard to its use with a bi-leaflet mechanical heart valve which has an annulus with a substantially annular aperture. Such a heart valve prosthesis is available from St. Jude Medical, Inc. of St. Paul, Minn. However, the invention is applicable to other types of heart valves as well.

Figure 1:
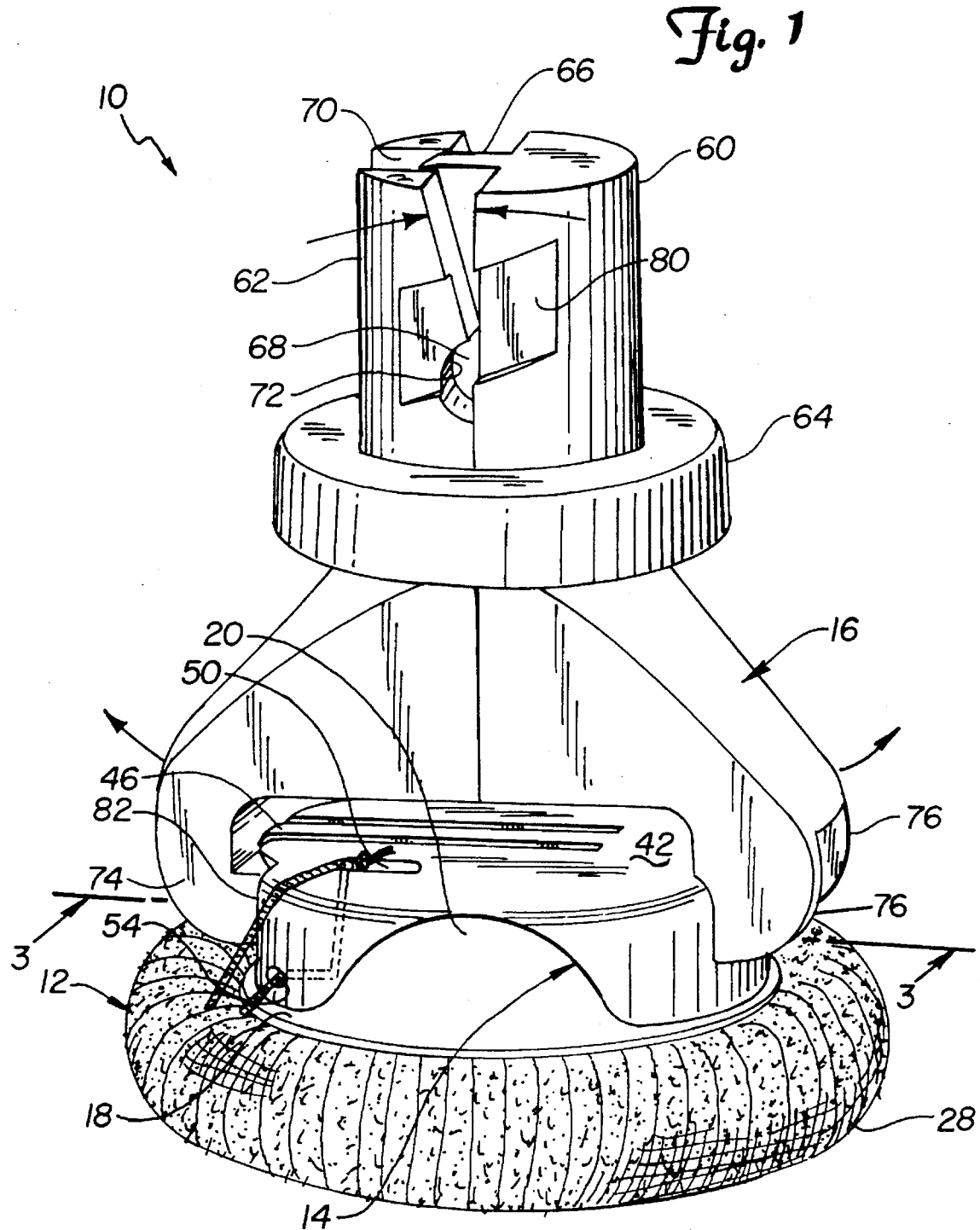
FIG. 1 is as perspective view of an assembly including a low profile mitral valve holder in accordance with one embodiment.
Figure 2:
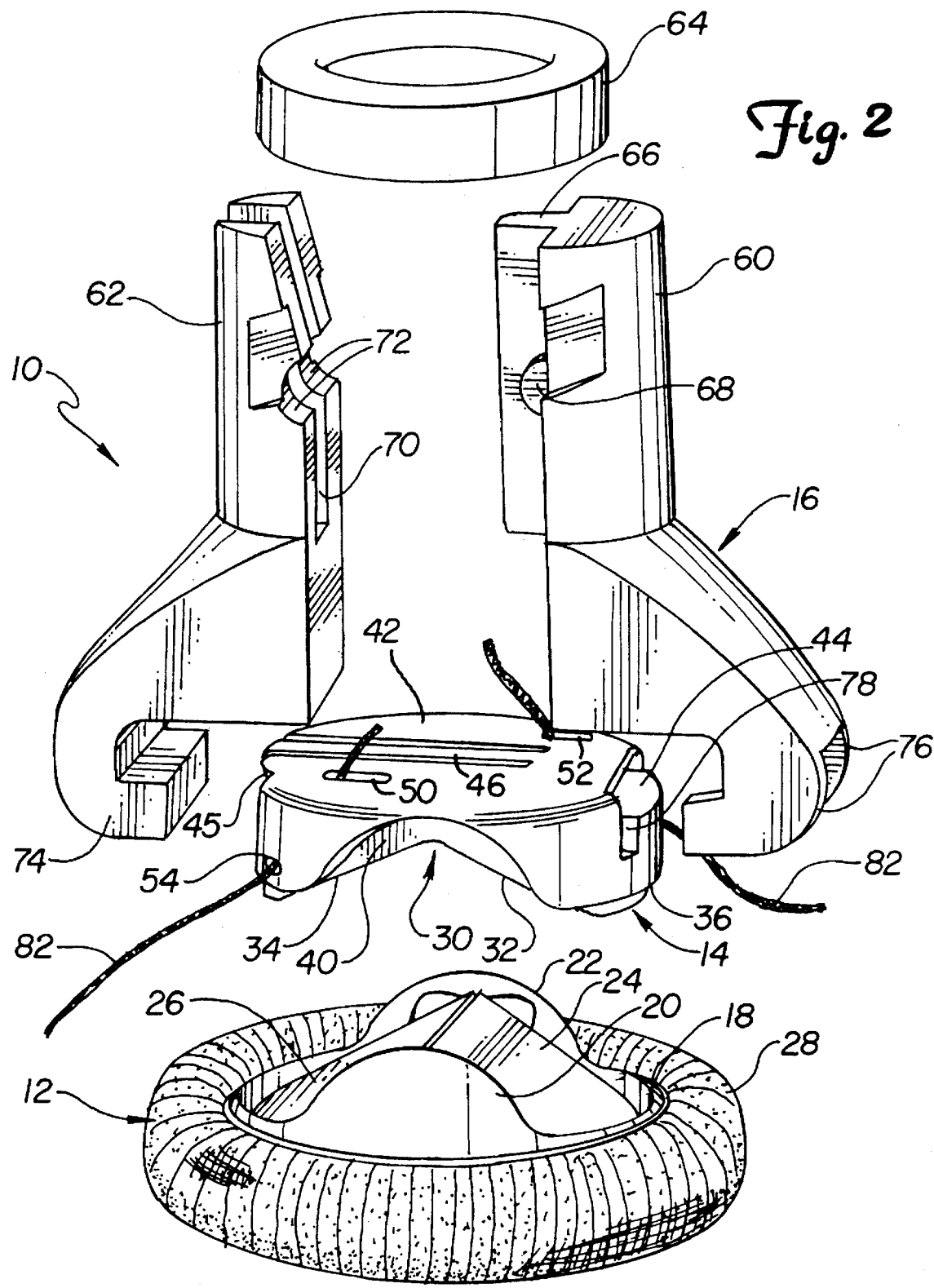
FIG. 2 is an exploded perspective view of the assembly of FIG. 1.

FIG. 1 is a perspective view and FIG. 2 is an exploded perspective view, respectively, of an assembly 10 which includes mitral heart valve prosthesis 12, heart valve holder 14 and hanger 16. Valve 12 includes valve orifice 18 having leaflet pivot guards 20 and 22 which support leaflets 24 and 26. A sewing ring or suture cuff 28 surrounds the outer radius of orifice 18.

Figure 3:
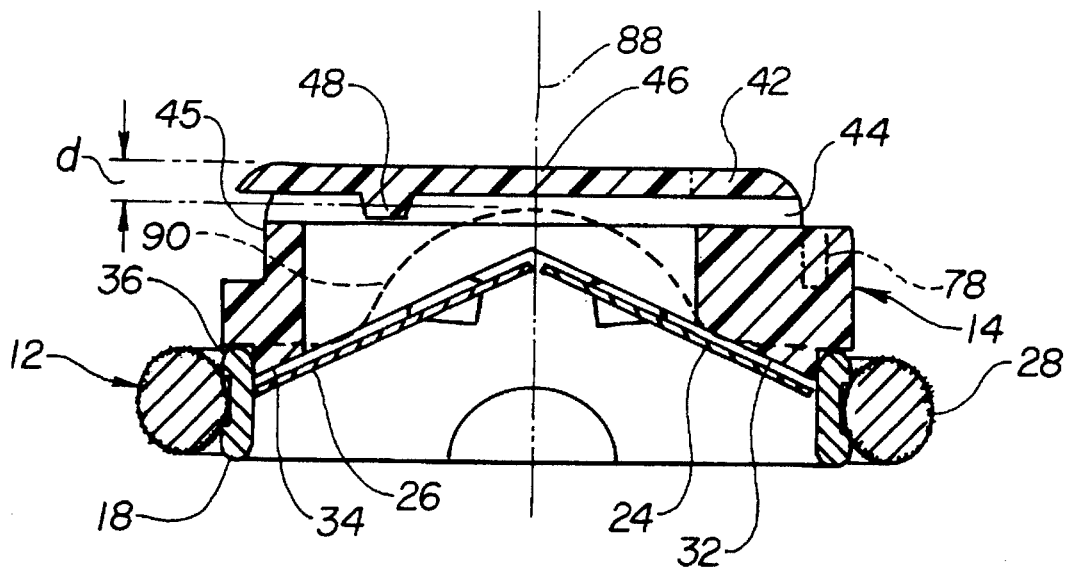
FIG. 3 is a cross-sectional view of the valve holder and valve of FIG. 1 taken along line 3—3.

Holder 14 includes distal surface 30 which provides leaflet conforming surfaces 32 and 34 adapted for receiving a proximal side of valve 12. A radial lip 36 extends around the outer circumference of distal surface 30 and conforms to valve orifice 18. Holder 14 includes pivot guard receiving portion 40 adapted for receiving pivot guard 20 (or 22). Holder proximal surface 42 is a planar surface which is substantially parallel with the annulus of valve 12 and perpendicular to the axis 88 of valve 12, as shown in FIG. 3. Surface 42 is positioned proximate pivot guards 20 and 22 to provide an overall low profile to holder 14 as viewed from the side. Surface 42 overlies slot 44 and includes cantilever arm 46 which carries tab 48 (shown in FIG. 3). Surface 42 includes suture holes 50,52 and the outer radius of holder 14 includes suture holes 54.

Hanger 16 includes holder stems 60 and 62 and collar 64 which holds stems 60 and 62 together when hanger 16 is assembled onto holder 14. Tab 66 extends outwardly from stem 60 adjacent pivot 68. Stem 62 includes slot 70 for receiving tab 66 and pivot receptacle 72 for receiving pivot 68. Leg 74 of stem 62 fits in slot 45 of holder 14 and legs 76 of stem 60 fit in downward extensions 78 of slot 44. Hanger 16 is adapted for suspending holder 14 and valve 12 at notch 80 in packaging (not shown) during transportation and prior to implantation. Holder 14 is removed from hanger 16 by removing collar 64 from stems 60 and 62 such that stems 60 and 62 rotate about pivot 68 as shown by the arrows in FIG. 1. Holder 14 is secured to valve 12 by sutures 82 which extend through holes 50 and 54 of holder 14 and through cuff 28 of valve 12.

FIG. 3 is a cross-sectional view of valve 12 and valve holder 14 taken along a plane parallel with the axis 88 of valve 12 along line 3—3 in FIG. 1. Dashed line 90 in FIG. 3 indicates the position of the most proximal surface of valve 12. As shown in FIG. 3, the distance d between proximal surface 42 of holder 14 and proximal surface 90 of valve 12 is designed to be relatively small. Further, surfaces 32 and 34 of holder 14 maintain leaflets 24 and 26 in a closed position such that they do not protrude from valve 12. This configuration provides a significantly lower profile for the valve/holder assembly than in typical prior art designs. By providing a reduced profile, heart valve 12 is more easily inserted into a patient through a trocar between the ribs or other small opening in a patient. Further, leaflets 24 and 26 are protected by valve orifice 18 during implantation and do not extend below valve 12. This prevents leaflets 24 and 26 from being damaged as heart valve 12 is inserted through the trocar.

Figure 4:
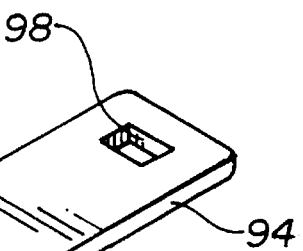
FIG. 4 is a perspective view of a handle for attachment to the holder shown in FIGS. 1 through 3.

FIG. 4 is a perspective view of handle 91 which includes elongated grip 92 coupled to flat distal end portion 94. Distal portion 94 includes opening 98. Handle 91 is adapted to couple to valve holder 14 by insertion into slot 44. Tab 48 is forced into opening 98 of handle 91 by spring loaded arm 46, thereby releasably securing handle 91 to holder 14. Handle 91 is disengaged by lifting arm 46 while removing distal portion 94 from slot 44.

During implantation, the surgeon removes assembly 10 from the packaging (not shown). Hanger 16 is removed from holder 14 by removing collar 64 and squeezing the proximal end of hanger 16 together. This causes legs 74, 76 to pivot about pivot 68 thereby freeing holder 14. Distal end 94 of handle 91 is inserted into slot 44 and locked into place by tab 48 in opening 98. This may be done before removing hanger 16 from packaging or before removing holder 14 from hanger 16. Leaflets 24 and 26 are protected within orifice 18 during insertion. The valve 12 is inserted through the trocar and is secured to the heart tissue annulus. After valve 12 is secured to the tissue annulus of the heart, holder 14 is then removed by cutting sutures 82 and removing handle 91 and holder 14 from the patient.

Figure 5:
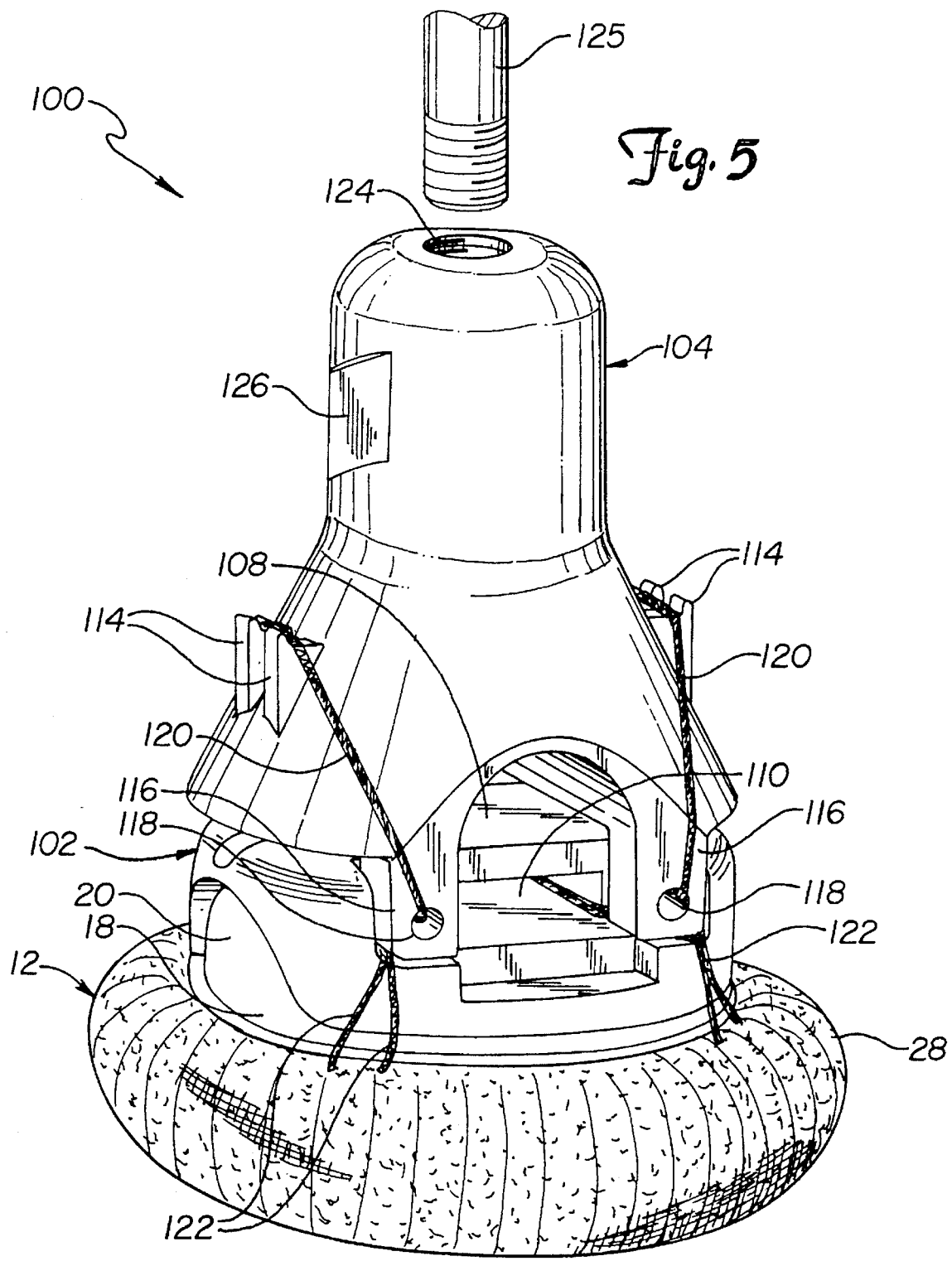
FIG. 5 is a perspective view of an assembly including a valve holder in accordance with another embodiment.
Figure 6:
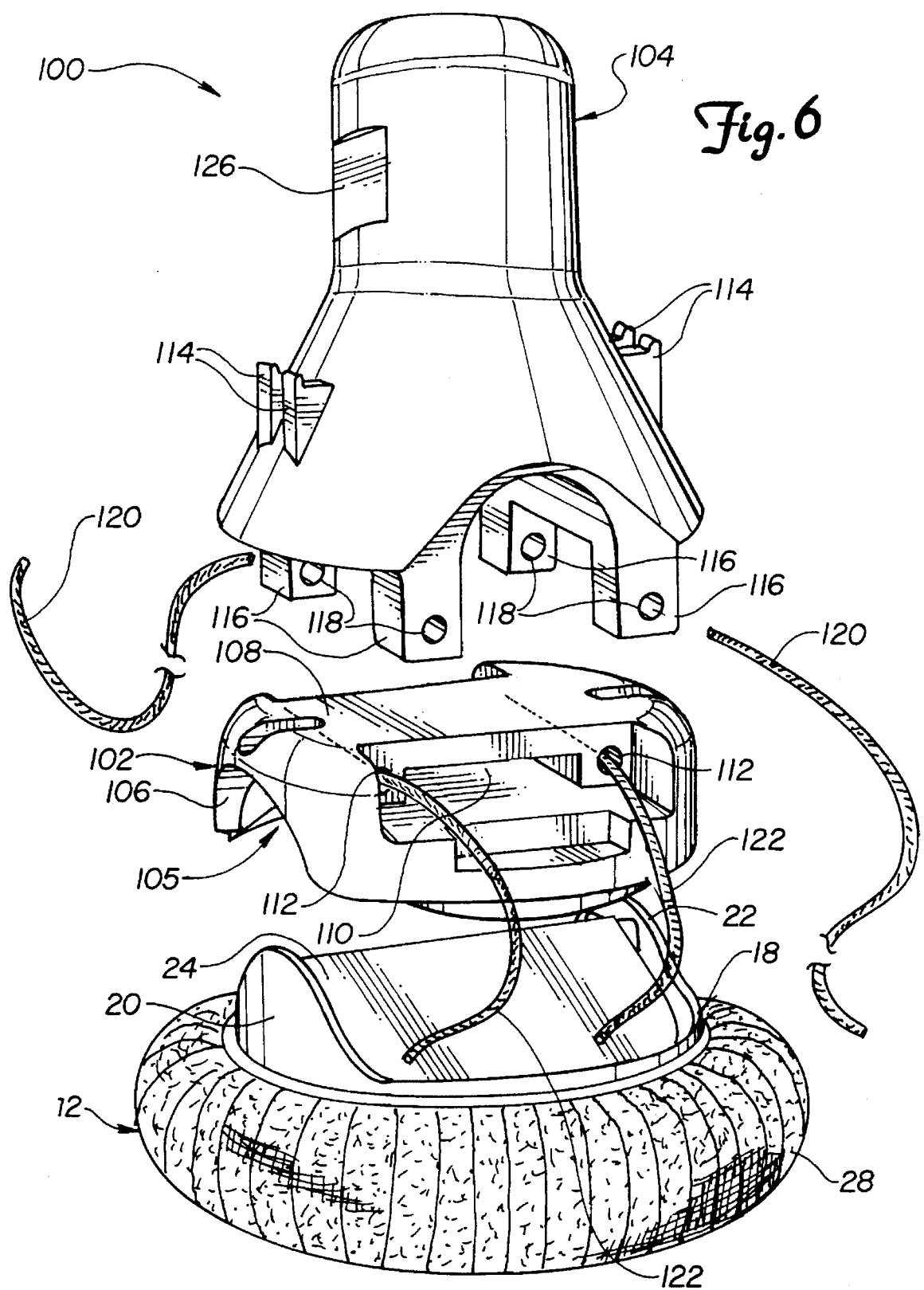
FIG. 6 is an exploded perspective view of the assembly of FIG. 5.

FIGS. 5 and 6 show a perspective view and an exploded perspective view, respectively, of assembly 100 in accordance with another embodiment. Assembly 100 includes holder 102 coupled to valve 12 supported by hanger 104 in the packaging (not shown). A distal engaging surface 105 of holder 102 is similar to surface 30 shown for holder 14 in FIGS. 1 through 3. Holder 102 includes pivot guard receiving portions 106 and proximal surface 108. A slot 110 and suture openings 112 extend through holder 102 perpendicular to the axis of valve 12.

Hanger 104 includes suture shoulders 114 and legs 116 having suture openings 118. Sutures 120 extend through holes 118 of hanger 104 and through holes 112 of holder 102 thereby securing hanger 104 to holder 102. Sutures 122 extend through holes 112 of holder 102 and through cuff 28 of valve 12 thereby securing holder 102 to valve 12. Hanger 104 includes threaded receptacle 124 and slot or notch 126. Notch 126 is used to suspend hanger 104 from packaging (not shown) during transportation prior to implantation of valve 12. Threaded receptacle 124 is optionally used to receive a threaded handle 125 to facilitate removal of assembly 100 prior to implantation.

Assembly 100 is used in a manner similar to that described for assembly 10. The surgeon removes the assembly from the packaging (not shown). A handle is inserted into slot 110. Alternatively, the handle may be inserted into assembly 100 before removing assembly 100 from the packaging. Sutures 120 are cut such that holder 102 may be removed from hanger 104. The implantation procedure proceeds as described above. After valve 12 has been sutured to the patient's heart, sutures 122 are cut and holder 102 is removed.

Figure 7:
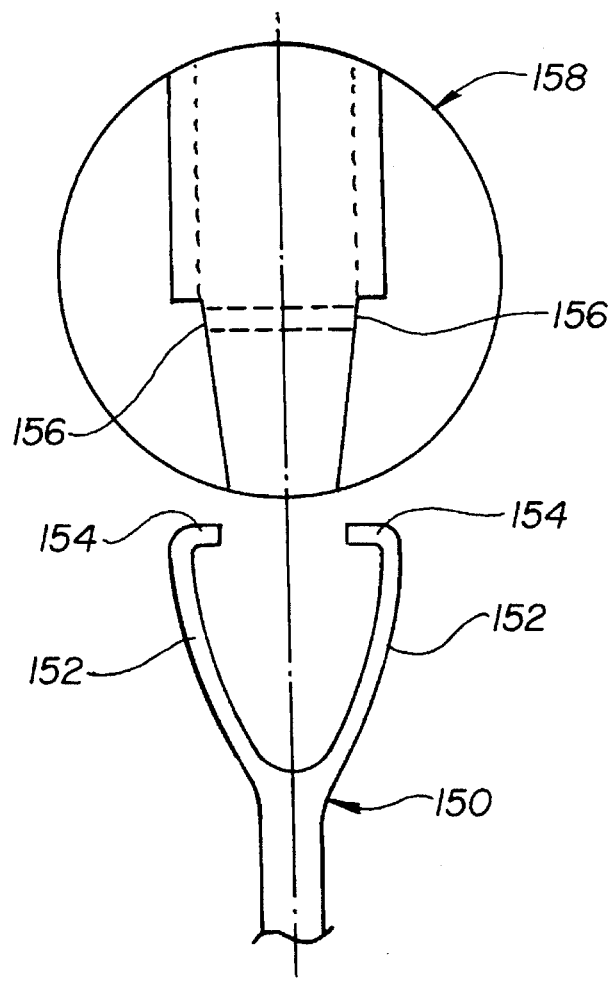
FIG. 7 is a top plan view of a handle and holder in accordance with one embodiment.
Figure 8:
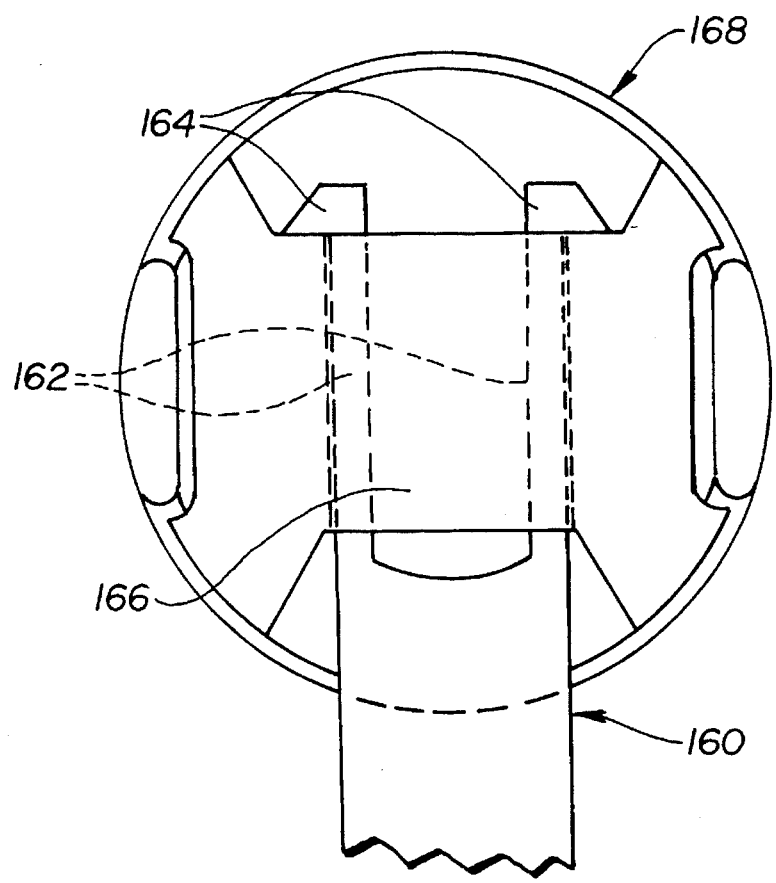
FIG. 8 is a top plan view of a holder and handle in accordance with another embodiment.

FIGS. 7 and 8 are top plan views showing two additional embodiments for attaching the handle to the low profile holders described herein. In FIG. 7, handle 150 includes distal legs 152 each having a tip 154. Openings 156 are provided in holder 158. Openings 156 receive tips 154 such that handle 150 is secured to holder 158. Handle 150 is attached by urging tips 154 toward openings 156 until they engage openings 156. Handle 150 can be removed by spreading tips 150 in an outward direction to disengage openings 156. As shown in FIG. 7, handle 150 is substantially perpendicular to the axis of holder 158 but can pivot relative to holder 158 in opening 156 such that handle 150 is substantially coaxial with the axis of valve 12.

FIG. 8 shows another embodiment in which a handle 160 includes legs 162 each carrying a tab 164. Legs 162 are received in slot 166 of holder 168, as shown in FIG. 8. Tabs 164 lock handle 160 into holder 168 as handle 160 is inserted into slot 166. Removal is by squeezing tabs 164 together.

Figure 9:
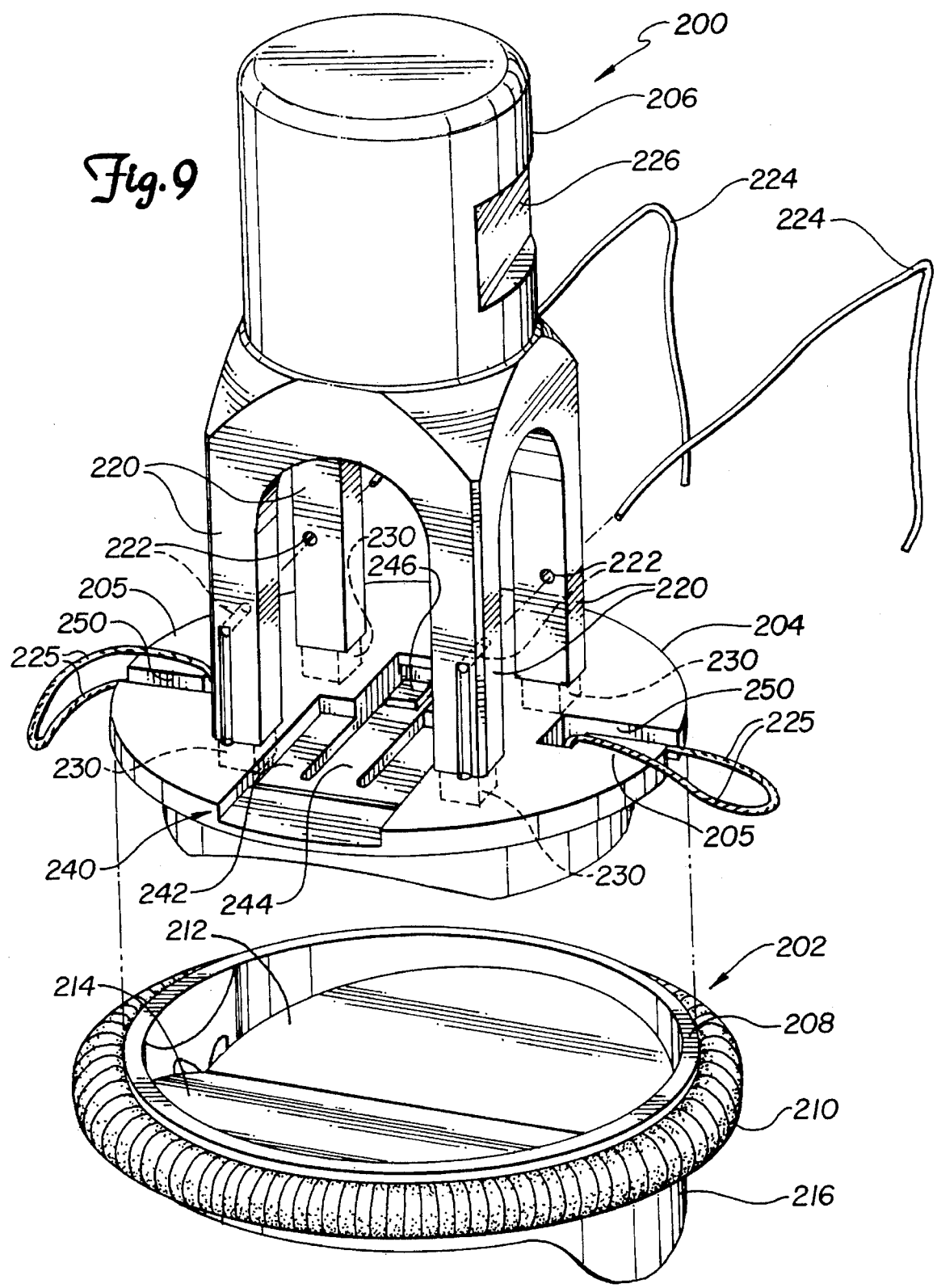
FIG. 9 is a partially exploded perspective view of another embodiment.

FIG. 9 is a perspective partially exploded view of assembly 200 in accordance with another embodiment. Assembly 200 is adapted for use with aortic heart valve prosthesis 202 and includes holder 204 and hanger 206. Aortic valve 202 includes valve orifice 208, cuff 210, leaflets 212 and 214 protected by leaflet pivot guard 216. Hanger 206 includes hanger legs 220 having suture holes 222 to receive sutures 224. Hanger 206 includes notch 226 adapted for being held in packaging (not shown).

Holder 204 includes hanger leg receptacles 230 adapted for receiving hanger legs 220 of hanger 206. Hanger 206 is attached to holder 204 with sutures 224 which extend through holes 222 and holder 204. Holder 204 attaches to valve 202 with sutures 225, shown in more detail in FIG. 10. Holder 204 includes handle receptacle 240 which includes recessed area 242 and cantilever 244 which carries tab 246. Holder 204 is attached to valve 202 by passing a suture 225 through cuff 210. One portion of suture 225 lies within groove 250 and the other portion of suture 225 lies on holder proximal surface 205. The ends of suture 225 are then wrapped around protrusion 251 within groove 250 and knotted. The recessed suture opening reduces the likelihood that both ends of suture 225 projecting from cuff 210 are unintentionally severed by the surgeon, thus reducing the possibility of a portion of suture 225 being inadvertently left within the patient's heart.

Figure 10:
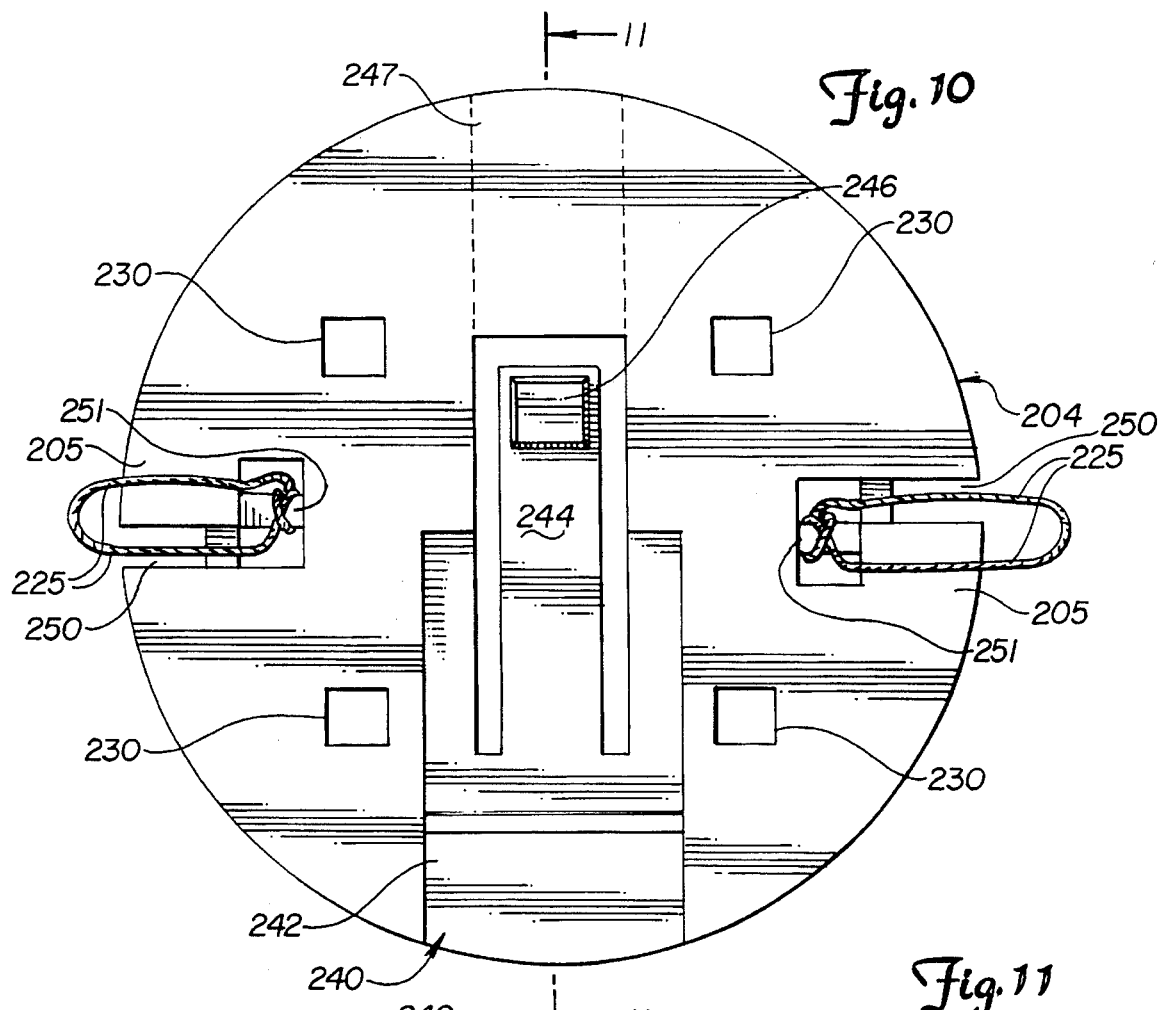
FIG. 10 is a top plan view of a valve holder shown in FIG. 9.

FIG. 10 is a top plan view of low profile aortic valve holder 204. The plan view of FIG. 10 shows suture grooves 250 which are recessed in holder 204 and adapted for receiving sutures 225. The recessed suture grooves 250 provide a further reduction in the profile of holder 204. Holder 204 includes opening 247 which facilitates manufacture using injection molding techniques.

Figure 11:
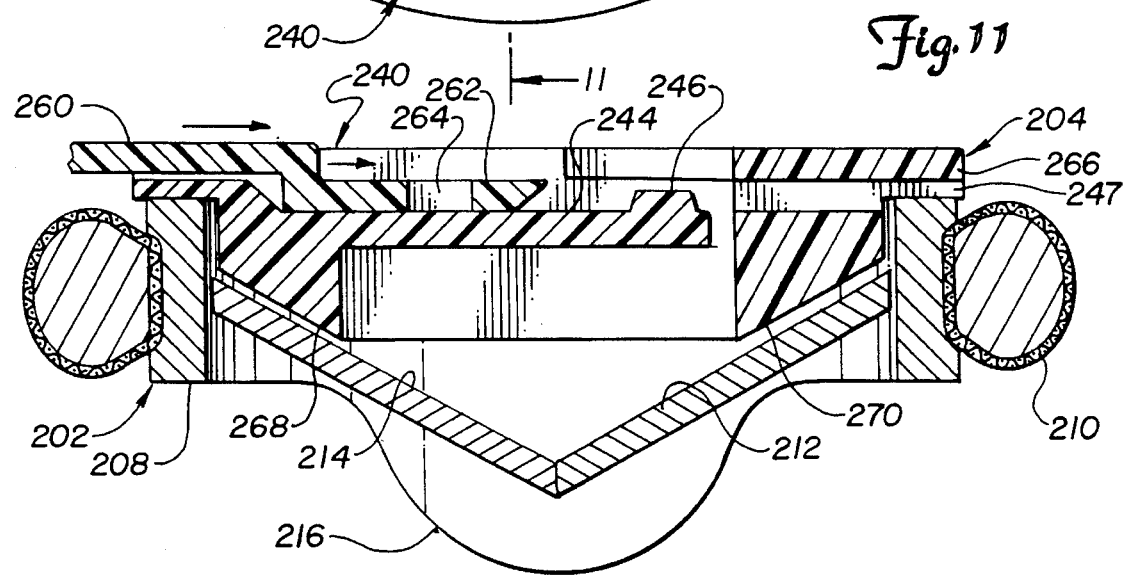
FIG. 11 is a cross-sectional view of a handle and heart valve, and the holder shown in FIG. 10.
Figure 12:
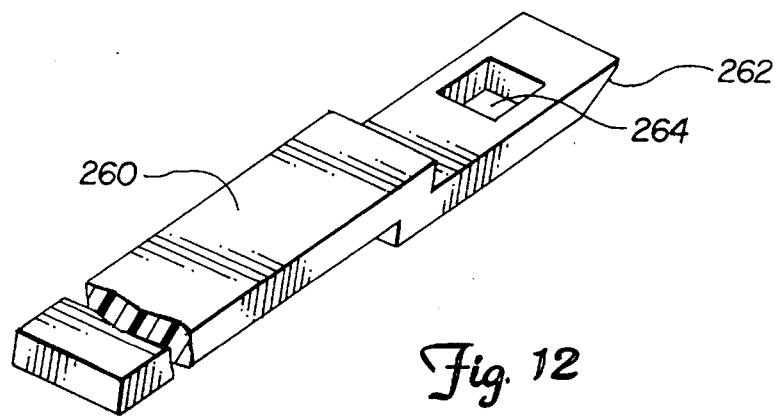
FIG. 12 is a perspective view of a handle shown in cross section in FIG. 11.

FIG. 11 is a cross-sectional view of holder 204, taken along the line labeled 11—11 in FIG. 10, and handle 260 and valve 202, shown prior to operational engagement with valve 202. FIG. 11 also shows handle 260 partially in receptacle 240 and prior to engagement of tab 246 into opening 264 in handle 260. Handle 260 is attached by insertion of end 262 into receptacle 240. FIG. 12 is a perspective view of handle 260. Handle 260 includes distal end 262 having opening 264. The tip of distal end 262 is beveled to push tab 246 downward as distal end 262 is slid along cantilever 244 after insertion into opening 240 so that tab 246 is received in opening 264, thereby locking handle 260 to holder 204. As shown in FIG. 11, holder 204 includes lip 266 which extends around valve orifice 208. The distal side of holder 204 is adapted for interfacing with the proximal side of valve 202 and includes leaflet conforming surfaces 268 and 270 which are positioned adjacent leaflets 214 and 212, respectively. A minimal gap is maintained between leaflets 214 and 212 and surfaces 268 and 270 to prevent the leaflets from being damaged. However, surfaces 268 and 270 are shaped generally to retain leaflets 214 and 212 in a closed position. As discussed above, this helps maintain a low profile for holder 204 and valve 202.

Figure 13:
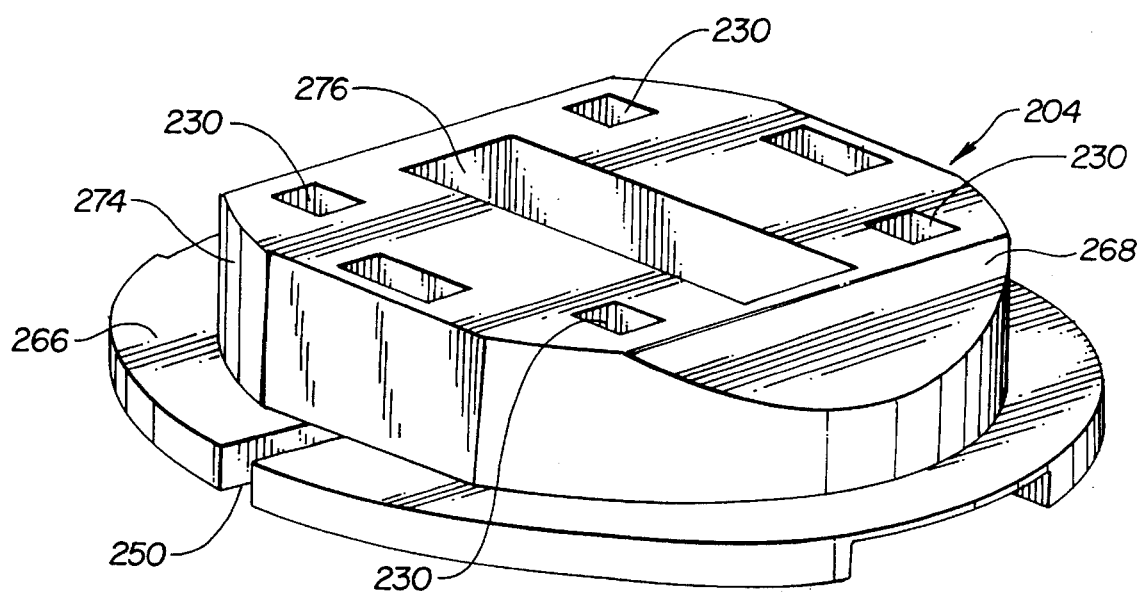
FIG. 13 is a distal perspective view of the holder of FIGS. 10 and 11.

FIG. 13 is a perspective view showing the distal side of valve holder 204. FIG. 13 clearly shows lip 266 which engages valve orifice 208. Generally, the only portion of holder 204 which extends above valve orifice 208 is lip 266. The main body portion 274 of holder 204 is carried within valve orifice 208, as shown in FIG. 11.

FIG. 14 is a perspective view of aortic valve holder 300 for use with valve 202 in accordance with another embodiment. FIG. 14 shows the proximal side of holder 300 which includes attachment (locking) ring 310 carried on upper surface 312 and which includes lip 314. Lip 314 is adapted for engagement with valve orifice 208, shown in FIG. 11. Holder 300 includes main body portion 316 which is received within valve orifice 208. Leaflet conforming surfaces 318 and 320 are adapted for maintaining leaflets 214 and 212 in a closed position, as shown in FIG. 11.

Attachment ring 310 is adapted for attachment to handle 330, shown in FIG. 15. Handle 330 includes distal locking element 332 and proximal locking element 334. Elements 332 and 334 are supported between elongated member 336.

Figure 16:
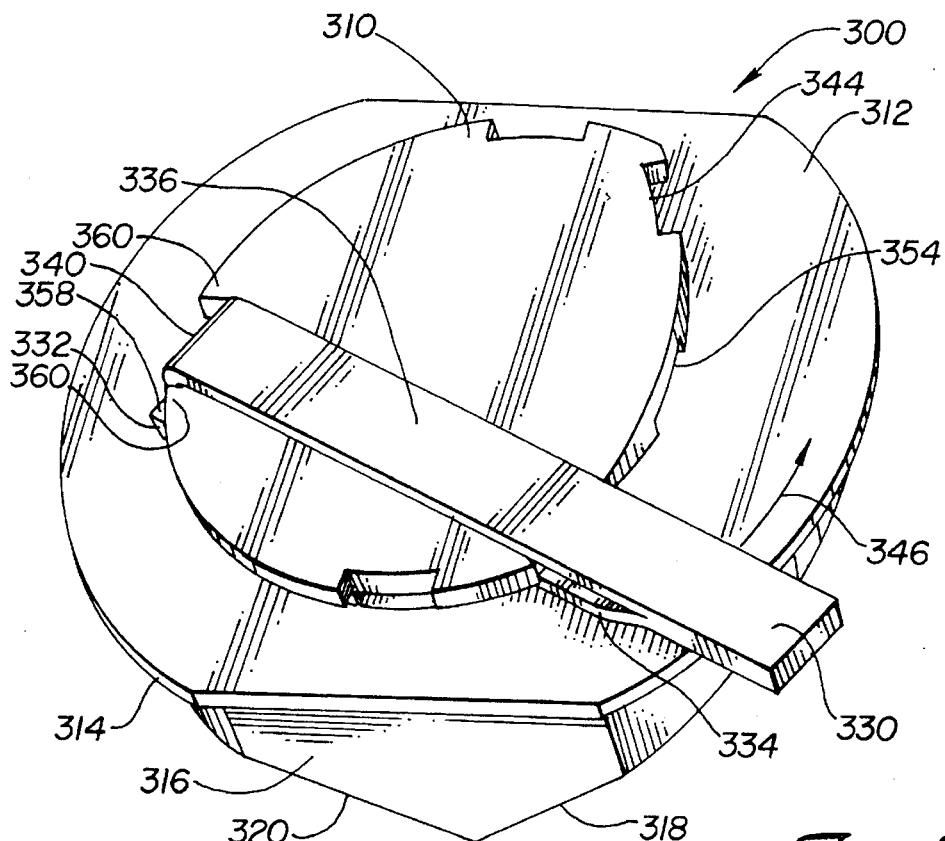
FIGS. 16 and 17 are top perspective views showing attachment of the handle of FIG. 15 to the holder of FIG. 14.
Figure 17:
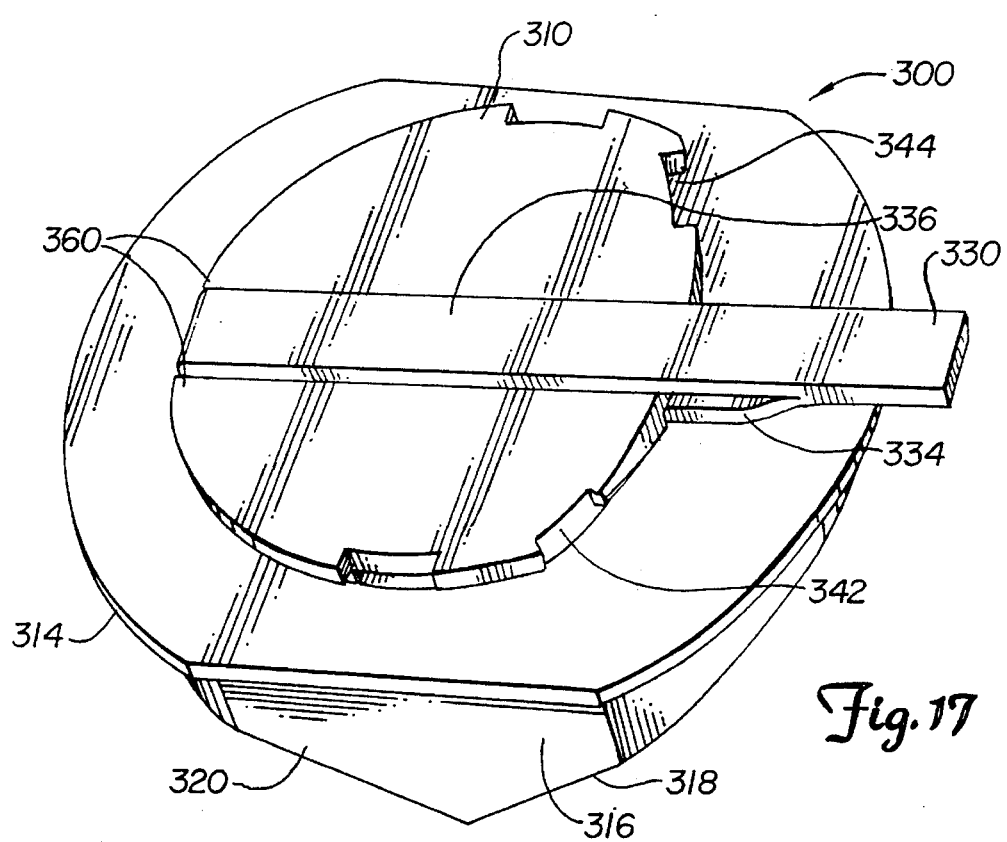

FIGS. 16 and 17 are perspective views showing the steps of locking handle 330 to holder 300. As shown in FIG. 16, distal locking member 332 is placed in distal receptacle 340 while proximal locking member 334 is placed through opening 342 of attachment ring 310 so it is positioned below the lead-in end of ramp 352 (FIG. 14). Opening 344 is similar to opening 342. Handle 330 is then moved in the direction shown by arrow 346 in FIG. 16 to the position shown in FIG. 17. This causes proximal locking member 334 to slide through groove 350, shown in FIG. 14, under and along ramp 352. As handle 330 completes movement to the position shown in FIG. 17, proximal locking member 334 resiliently snaps into locking recess 354 thereby locking handle 330 in position. Note that distal tab 358 is locked under lip 360 of locking ring 310. Thus, both distal locking member 332 and proximal locking member 334 of handle 330 are securely fastened to locking ring 310. This provides two solid points of attachment positioned on opposite sides of the annulus of valve 202. Handle 330 is removed by spreading locking member 334 outwardly such that locking recess 354 is disengaged and handle 330 may be rotated and removed in a manner opposite to that described above.

Figure 18:
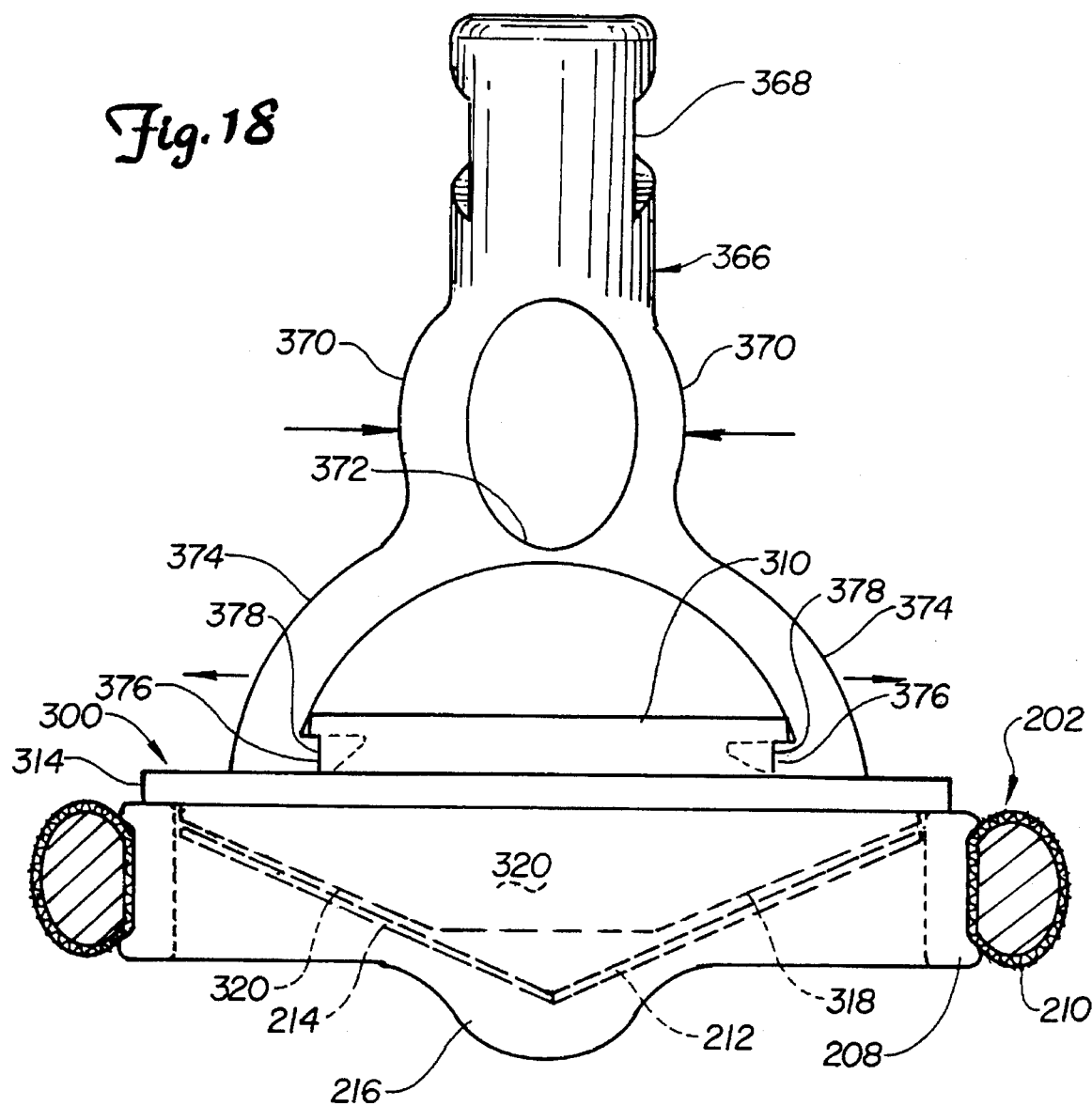
FIG. 18 is a plan view of a hanger adapted for engaging the holder of FIGS. 14, 16 and 17.

FIG. 18 is a plan view of hanger 366 adapted for carrying holder 300, or one or more of the holder embodiments shown herein, and attachment to packaging (not shown). For illustrative purposes, valve 202 is shown in cross section. Hanger 366 includes notches 368 adapted for attachment to packaging (not shown), release points 370, pivot 372 and legs 374. Each leg 374 includes tab 376 at its distal end which is adapted to be received in openings 378 of holder 300. Application of pressure to points 370 in the direction shown by the arrows causes legs 374 to spread apart outwardly thereby releasing tabs 376 from openings 378 in holder 300. In one embodiment, a locking member such as a bar extending between points 370 prevents holder 300 from inadvertently being released from hanger 366 by application of pressure to points 370. Such a locking member can be removed or cut at the appropriate time to allow release of holder 300.

Figure 19:
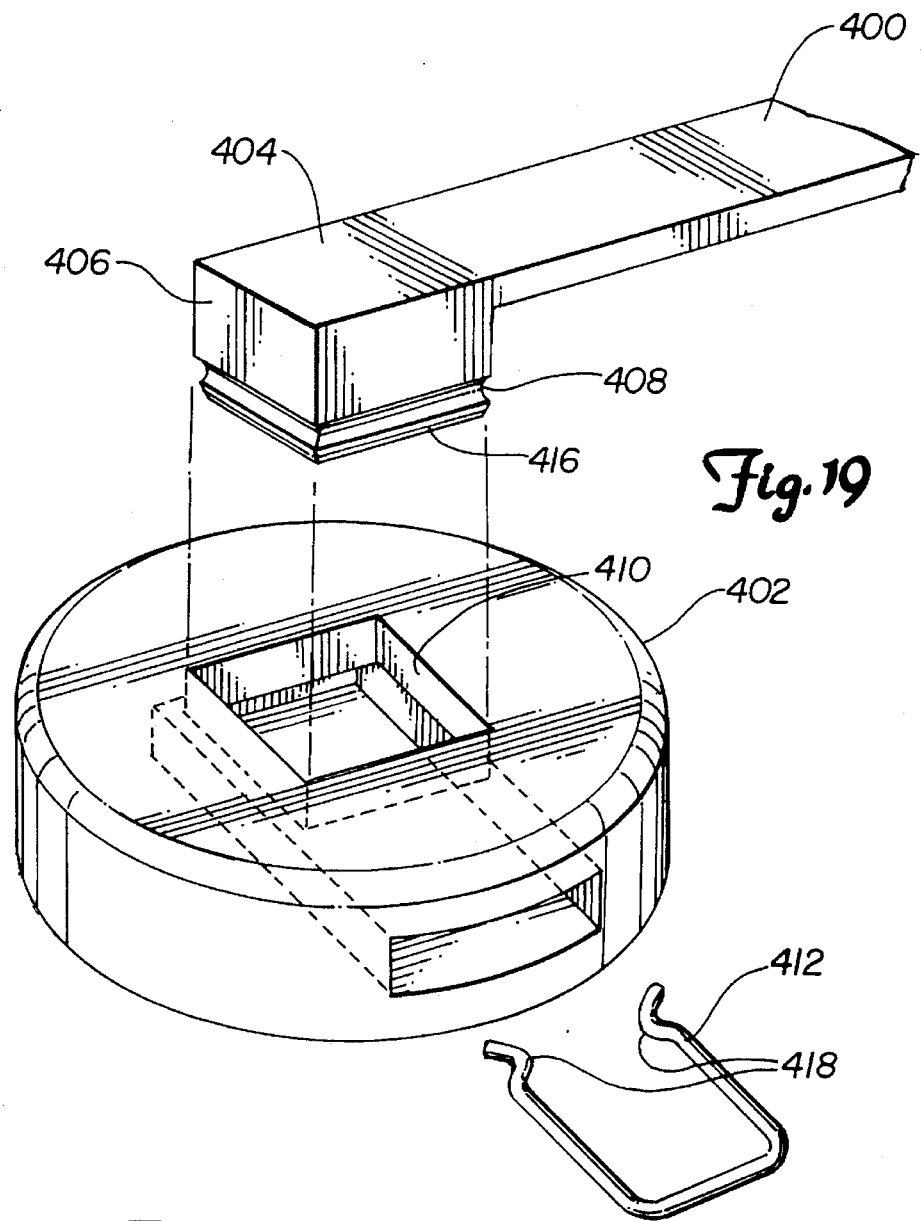
FIG. 19 is an exploded perspective view showing attachment of a handle to a holder in accordance with another embodiment.
Figure 20:
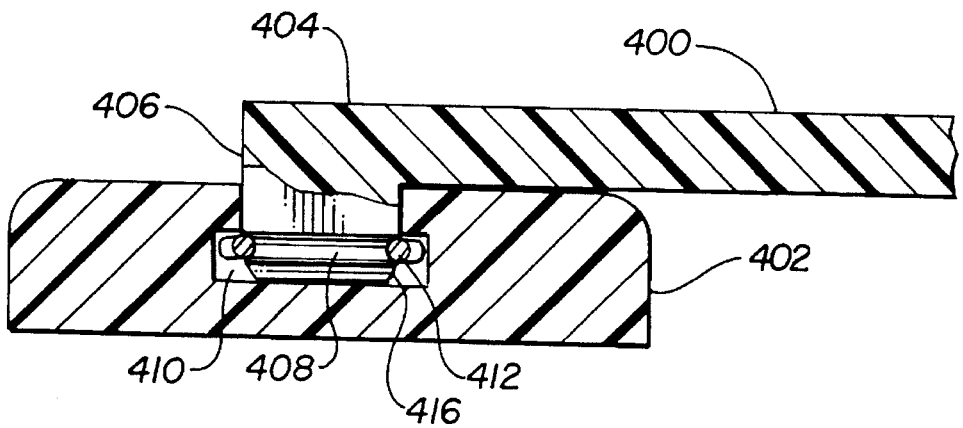
FIG. 20 is a cross-sectional view of the holder and handle of FIG. 19.

FIGS. 19 and 20 are perspective and cross-sectional views, respectively, of another embodiment for attaching a handle 400 to a valve holder shown generally at 402. Distal end 404 of handle 400 includes attachment portion 406 having groove 408 formed therein. Holder 402 includes opening 410 which carries spring loaded locking clip 412 which is typically any material with sufficient spring properties, such as metals or polymers, such as a formed spring material, shape memory material, a metal or a polymer. Locking clip 412 is held in holder 402. Attachment portion 406 is urged downward into opening 410. Beveled (or chamfered) section 416 causes tips 418 of clip 412 to be spread apart in an outward direction. Once locking portion 406 has fully entered opening 410, tips 418 lock into groove 408 thereby securing handle 400 to holder 402. Handle 400 is removed by simply pulling it out of opening 410.

FIGS. 21 and 22 are perspective and cross-sectional views, respectively, of another embodiment of the invention for attaching handle 400 to low profile valve holder shown generally at 430. Holder 430 includes opening 432 for receiving attachment portion 406. Opening 432 carries attachment clip 434 having ridges 436 adapted for engaging groove 408. Handle 400 is removed by simply pulling it from opening 432.

In general, the materials used herein are materials suited for the biomedical industry. For example, the holder can be made of a polymer such as a polysulfone, known under the trade name of Udel®, or other similar biocompatible durable material, and is suitable for forming by injection molding or other manufacturing methods. Typical materials for the handle include stainless steel, or other biocompatible metals or polymers. In the embodiment of handle 330 shown in FIG. 15, a suitable spring material is desirable such as cobalt chrome or cobalt nickel alloys, stainless steel, or a polymer such as polysulfone. The embodiments shown in FIGS. 19 through 22 allow for ease of disengagement of the handle from the holder following removal of the holder from the patient. Additionally, all designs tend to allow easy attachment of the handle to the holder during surgery while maintaining the sterile condition of the pieces. Injection molding techniques are well suited for fabricating the low profile holder set forth herein. A suitable distance between a leaflet and a leaflet conforming surface is maintained so as to not apply pressure to the leaflets during transportation or use of the valve while attached to the low profile holder. This stabilizes the leaflet without substantial contact to the leaflet which could damage the leaflet. Furthermore, the holder set forth herein provides a guard to prevent the handle from contacting the valve during use. One aspect of the invention includes placing the handle in close proximity with the valve and in a plane parallel with the valve annulus to reduce the height of the valve/holder assembly.

The invention as set forth herein securely attaches the holder to the valve and the valve to the handle or hanger as one integral piece until the sutures are cut. The low profile design allows easy and safe manipulation of the valve in a surgical environment and during implantation. Easy engagement (and disengagement) of the holder and handle assembly is provided which has advantages including speed, ease, safety and effectiveness in a surgical environment. The integral packaging allows the entire assembly to be sterilized as a unit. The various elements are provided for easy manufacture using injection molding techniques. Protection of the leaflets within the valve orifice is maintained. Additionally, the low profile design allows for use of minimally invasive surgical techniques which will promote more rapid patient recovery.

Although the present invention has been described with reference to preferred embodiments, workers skilled in the art will recognize that changes may be made in form and detail without departing from the spirit and scope of the invention.

What is claimed is:

1. A device for engaging during implantation a heart valve prosthesis having an annulus defining a plane with a substantially annular aperture therein and at least one leaflet movable between an open position and a closed position, the device comprising:

a handle having a proximal end and a distal end; and a low profile holder coupled to the distal end of the handle and having a proximal surface and a distal engaging surface adapted for engaging the heart valve prosthesis and shaped for maintaining the at least one leaflet in a closed position during implantation wherein the proximal surface and the handle are substantially parallel to the plane of the annulus and the distal end of the handle is adjacent the heart valve prosthesis.

2. The device of claim 1 including a suture connecting a suture cuff of the heart valve prosthesis to the low profile holder.

3. The device of claim 2 wherein the holder includes an opening for receiving the suture therethrough.

4. The device of claim 1 wherein the heart valve prosthesis is a mitral heart valve prosthesis having a proximal side carrying first and second leaflet pivot guards and a distal side, wherein the distal engaging surface of the holder conforms to the proximal side of the valve prosthesis when the leaflet is in the closed position and is positioned between the first and second pivot guards.

5. The device of claim 4 wherein the distal engaging surface of the holder is proximate the first and second pivot guards.

6. The device of claim 1 wherein the heart valve prosthesis is an aortic heart valve prosthesis having a proximal side and a distal side, wherein the distal engaging surface of the holder conforms to the proximal side of the heart valve when the leaflet is in the closed position and extends into the annular aperture.

7. The device of claim 6 wherein the distal engaging surface of the holder is adjacent the proximal side of the heart valve.

8. The device of claim 1 wherein the low profile holder includes an attachment mechanism adapted for receiving the distal end of the handle.

9. The device of claim 8 wherein the attachment mechanism includes a slot defined in the holder for receiving the distal end of the handle.

10. The device of claim 9 wherein the attachment mechanism includes a cantilever carrying a tab urged into an opening in the handle thereby securing the handle to the holder.

11. The device of claim 8 wherein the attachment mechanism includes a clip carried in the holder for grasping the distal end of the handle.

12. The device of claim 1 including a hanger having first and second stems coupling to the low profile holder and a collar securing the first and second stems.

13. The device of claim 12 wherein the first and second stems include a pivot whereby the stems rotate about the pivot upon removal of the collar thereby releasing the holder.

14. The device of claim 1 including a hanger having legs for coupling to the holder, a pivot and a release point for application of pressure to spread the legs at the pivot thereby releasing the holder.

15. The device of claim 14 including a removable locking mechanism which prevents application of pressure to the release point from spreading the legs.

16. The device of claim 1 wherein the proximal surface of the low profile holder includes an attachment ring having a distal receptacle adapted for receiving a distal end of a handle and a proximal locking recess adapted for receiving a proximal locking member of the handle.

17. The device of claim 16 wherein the attachment ring includes an opening for receiving the distal locking member and a ramp adjacent the proximal locking recess for receiving the proximal locking member, whereby the proximal locking member slides from the opening across the ramp to engage the proximal locking recess.

18. A holder for holding a heart valve prosthesis during implantation through a trocar in a patient, the heart valve having an annulus forming a plane with a substantially annular aperture therein for carrying a leaflet, the holder comprising:

- a distal engaging surface conforming to the heart valve and the leaflet and of shape to maintain the leaflet in a closed position;
- a substantially flat proximal surface opposite the distal engaging surface and substantially parallel with the annulus;
- a handle attachment mechanism in the proximal surface comprising an opening in the holder for receiving a handle along an axis substantially parallel with the proximal surface and the plane of the annulus; and
- a releasable attachment to the heart valve prosthesis.

19. The holder of claim 18 wherein the releasable attachment comprises a suture extending through a suture cuff of the valve and coupled to the holder.

20. The holder of claim 18 wherein the heart valve prosthesis is a mitral heart valve prosthesis having a proximal side carrying first and second leaflet pivot guards and a distal side, wherein the distal engaging surface of the holder conforms to the proximal side of the valve prosthesis when the leaflet is in the closed position and is positioned between the first and second pivot guards.

21. The holder of claim 18 wherein the distal engaging surface of the holder is proximate the first and second pivot guards.

22. The holder of claim 18 wherein the heart valve prosthesis is an aortic heart valve prosthesis having a proximal side and a distal side carrying first and second leaflet pivot guards, wherein the distal engaging surface of the holder conforms to the proximal side of the heart valve when the leaflet is in the closed position and extends into the annular aperture.

23. The holder of claim 22 wherein the distal engaging surface of the holder is adjacent the proximal side of the heart valve.

24. The holder of claim 18 wherein the handle attachment mechanism includes a cantilever carrying a tab for engaging an opening in the handle thereby securing the handle to the holder.

25. The holder of claim 18 wherein the attachment mechanism includes a clip carried in the holder for grasping the handle.

26. The holder of claim 18 wherein the proximal surface includes an attachment ring having a distal receptacle adapted for receiving a distal end of a handle and a proximal locking recess adapted for receiving a proximal locking member of the handle.

27. The holder of claim 26 wherein the attachment ring includes an opening for receiving the distal locking member and a ramp adjacent the proximal locking recess for receiving the proximal locking member, whereby the proximal locking member slides from the opening across the ramp to engage the proximal locking recess.

* * * * *

UNITED STATES PATENT AND TRADEMARK OFFICE
Certificate

Patent No. 5,578,076                                  Patented: November 26, 1996

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Kurt D. Krueger, Stacy, MN; Guy Vanney, Blaine, MN; and Thomas F. Hinnenkamp, White Bear Lake, MN.

Signed and Sealed this Ninth Day of October, 2001.

CORRINE M. MCDERMOTT
                                                                                  *Supervisory Patent Examiner*
                                                                                         Art Unit 3738